United States Patent [19]

Schwartz

[11] 4,174,570
[45] Nov. 20, 1979

[54] MAGNETIC PIN SETTER USEFUL IN DENTISTRY

[76] Inventor: Donald E. Schwartz, 778 Crestway Dr., San Antonio, Tex. 78239

[21] Appl. No.: 815,701

[22] Filed: Jul. 14, 1977

[51] Int. Cl.² ............................................. A61C 13/00
[52] U.S. Cl. ........................................ 433/53; 433/74; 269/8
[58] Field of Search ................. 32/11, 40, 67, DIG. 6, 32/32; D13/99

[56] References Cited

U.S. PATENT DOCUMENTS

| 1,472,034 | 10/1923 | Asquith | 32/67 |
|---|---|---|---|
| 1,550,905 | 8/1925 | Kesling | 32/11 |
| 2,007,884 | 7/1935 | Spiro | 32/67 |
| 2,095,665 | 10/1937 | Greth | 32/67 |
| 2,534,023 | 12/1950 | Hirschhorn | 32/32 |
| 3,650,032 | 3/1972 | Kestler | 32/11 |
| 3,890,710 | 6/1975 | Jaeger | 32/11 |
| 4,017,972 | 4/1977 | Glenn | 32/11 |

Primary Examiner—Russell R. Kinsey
Assistant Examiner—John J. Wilson
Attorney, Agent, or Firm—Willard J. Hodges, Jr.

[57] ABSTRACT

A magnetic pin setter useful in constructing replicas of teeth for production of crowns and bridges. The device employs two support rods mounted on a base, each supporting a horizontal plate at its upper extremity. Mounted on the base between the two support rods is an adjustable work table. In producing castings for restoration work including crowns and bridges, dowel pins must be positioned for the casting and removal of individual tooth models to be restored. Small horseshoe magnets are magnetically attached to the horizontal plates and the second magnet interconnected to the first magnet holds a vertical support rod in position. The rods retain the dowel pins in position in the center of the individual teeth for the casting process.

6 Claims, 6 Drawing Figures

MAGNETIC PIN SETTER USEFUL IN DENTISTRY

BACKGROUND OF THE INVENTION

1. Field of the Invention

A mechanical magnetic pin setter for facilitating the positioning and retaining of dowel pins in the production of cast replicas of teeth and mouth to aid in the production of crowns and bridges for dental restoration.

2. Description of the Prior Art

Various mechanical devices have been developed and patented for performing functions in the area of this invention. One device utilizing permanent magnets in its construction is U.S. Pat. to Kestler, No. 3,650,032. The arrangement of the magnets and the related structure of Kestler, however, substantially varies from the combination of this invention. Several wholly mechanical devices not utilizing magnets have been developed and patented for the retention of dowel pins in position.

SUMMARY OF THE INVENTION

The device of this invention is designed to be supported on a desk or work bench to facilitate the dentist or technician in producing castings of the teeth as a procedure to assist the dentist in restoration procedures. The device generally comprises a rectangular base which may be constructed of formica or other suitable materials. Projecting upward from the base are two support rods which terminate in their upper extremity in two flat iron or steel metallic sheets comprising horizontal plates. Positioned below these horizontal plates substantially midway between the two vertical support rods is an adjustable work table. This work table is adjustable as to angle or tilt and elevation. The top of the work table has an adjustable plastic top supported by a ball and socket joint with the base of the work table securely attached to the base of the device. A ratchet shaft projects upward from the elevator base and is attached to the plastic top through the ball and socket interconnector. Knurled knobs connected to pinion drive shaft permits the elevation or lowering of the plastic top of the work table throughout a range of approximately 2 inches. The foregoing structure may be assembled from components presently commercially available; perhaps with the exception of the horizontal plates at the upper extremity of the support rods.

The most novel structure of this device perhaps resides in two interconnected permanent horseshoe magnets retained by a non-magnetic interconnecting yoke. The magnetic poles of the magnets are positioned and retained in the yoke in a 90° configuration or normal to the corresponding magnet. This pair of magnets with the interconnecting yoke formed the support structure from the horizontal plates to the metallic metal dowel support rods which retain the brass dowel pins at the exact desired position in the impression carried in the impression tray. The dowel pins are adjusted prior to casting exactly in the center of the tooth to be restored. The work table is then lowered by means of the pinion knurled knobs; the first pour of the castings is deposited in the impression carried by the impression tray and the work table returned to its previous position which is determined by the referenced pointer. The device is left in position until the casting sets. The first casting may be coated with a release agent and a second pour deposited to facilitate working with and separating of the cast impression. When the combined castings have solidified the individual tooth may be cut from the impression together with its dowel pin and worked with in preparation of crowns and bridges.

For a more detailed description of the construction and operation of the device reference is made to the attached drawings, the description of the preferred embodiment and the claims. Identical reference characters are utilized throughout the several drawings and detailed description to refer to identical or equivalent components.

DESCRIPTION OF THE PREFERRED EMBODIMENT

Figure 1:
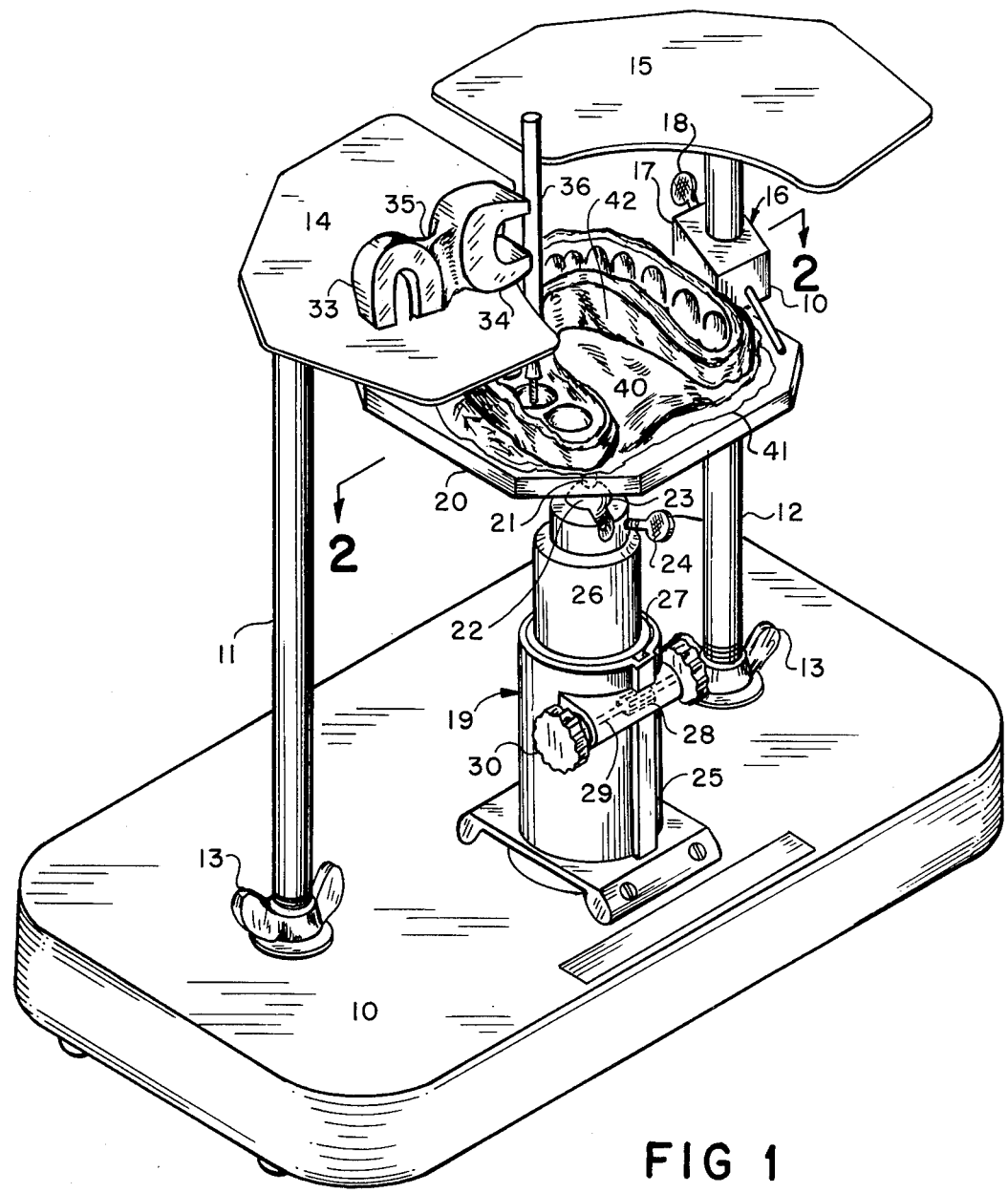
FIG. 1 is an elevation perspective view of the composite device simulating its use.
Figure 2:
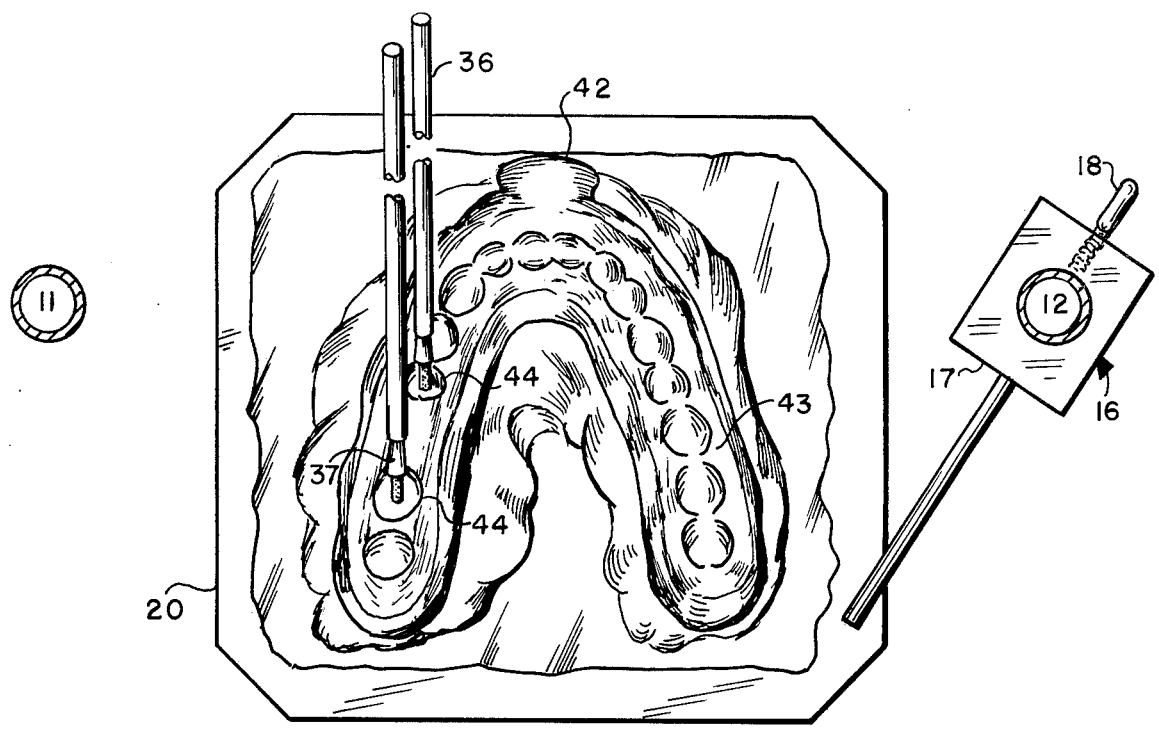
FIG. 2 is a top view taken on line 2—2 of FIG. 1 looking in the direction of the arrows illustrating dowel pins in positions in an impression for casting.
Figures 3, 4, 5:
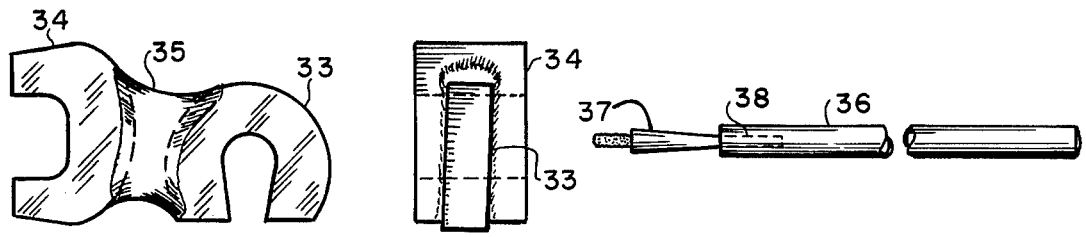
FIG. 3 is a fragmented view of the permanent magnets and their interconnecting yoke.
FIG. 4 is a fragmented view of the magnets rotated 90°.
FIG. 5 is a dowel support rod and brass dowel retained by the support rod.
Figure 6:
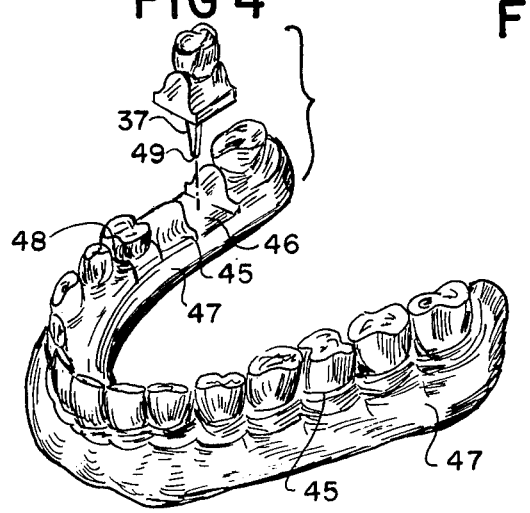
FIG. 6 is an exploded view of a final casting with a single tooth and dowel pin removed.

The preferred embodiment utilized a rectangular formica base 10 which was 1½ inches thick, 7 inches wide and 11 inches long. Equally spaced from each end of base 10 was a first support rod 11 and a second support rod 12. These rods 11 and 12 were ½ inch OD and 9½ inches long. The bottom portion was threaded and secured to the base 10 with rod securing nuts 13. The apertures in the base 10 receiving the support rods 11 and 12 were positioned 2 inches inward from each end of the base 10. At the upper extremity of each support rod 11 and 12 was welded a first horizontal support plate 14 and a second horizontal support plate 15. These plates 14 and 15 might be of various configurations; however, in the preferred embodiment the plates were approximately 3 inches by 5½ inches having generally an arcuate configuration. It is desirable in the construction to mount a reference pointer 16 on one of the support rods 11 and 12. Reference pointer 16 had a 2½ inch elongated pointer projecting from a plastic pointer base 17 which was ¾ inch wide and 2½ inches long. The pointer base 17 is secured in position on support rod 11 or 12 by means of a pointer set screw 18.

Positioned approximately midway of base 10 slightly off center from the support rods 11 and 12 is an adjustable work table 19 having a plastic top 20 which is approximately 4½ inches by 5 inches and ¼ inch thick. Its support stem 21 projects downward from the plastic top. The stem has a circular 1 inch base and a stem approximately 1 inch long. The stem terminates in a ball 22 approximately ½ inch in diameter which fits into a socket 23 resulting in a ball and socket joint which permits a tilting and adjusting of the plastic top 20 of the work table 19. Rotatably mounted beneath socket 23 was ball set screw 24 which is adapted to rotate and secure the ball and socket joint in position. Bottom portion of work table 19 is a cylindrical structure securely screwed to base 10 which comprises elevator base 25. This elevator base 25 is approximately 1¾ inches in diameter and is approximately 2¾ inches in length. The ratchet shaft 26 projects through elevator base 25 in such a fashion as to permit the raising or lowering of plastic top 20 of the work table. Projecting outward on one side of ratchet shaft 26 was a threaded rack 27 approximately 2 inches in length providing a range of lowering and elevation of the ratchet shaft 26 of approximately 2 inches. Engaging rack 27 was the pinion gear 28 which was secured on a pinion drive shaft 29 having pinion knurled knobs 30 at each end. Pinion drive shaft 29 was approximately 2¾ inches in length having ¾ inch knurled knobs 30 at each end.

A magnetic structure of novel design was developed for utilization in conjunction with the horizontal plates 14 and 15 mounted at the upper extremity of support rods 11 and 12. The magnetic structure comprises a horizontal horseshoe magnet 33 approximately 5/16 inch thick having a length from its arc to its poles of approximately 13/16 inch with the width of the contact polar surface of 14/16 inch securely interconnected to a somewhat larger vertical horseshoe magnet 34. This vertical horseshoe magnet 34 was ¾ inch thick also having a length from its arc to its place of approximately 13/16 inch with a contact surface at the poles of approximately 1 inch. Interconnecting these two magnets in a right angle configuration was a non-metallic plastic magnet connecting yoke 35. This yoke 35 maintained the horizontal magnet 33 and the vertical magnet 34 in a space relationship of approximately ¼ inch with the poles of the respective magnets forming a 90° angle. In utilizing this combined magnetic structure the horizontal horsehoe magnet 33 contacts horizontal plate 14 or 15 supporting and retaining vertical horseshoe magnet 34 in a position substantially perpendicular to base 10. This configuration permits the positioning of the iron or steel dowel support rods 36 in both the vertical and horizontal plane to be retained in the established position. These dowel support rods are ⅛ inch in diameter and 3 inches long. Brass dowel pins 37 are retained frictionally in position by dowel pin recesses 38 formed in the end of the dowel support rods 36.

In utilization of the device of this invention in producing a cast for replica of the individual teeth a portion of quick set plaster 40 is placed in the center of plastic top 20 of work table 19. The quick set plaster 40 is covered with a thin plastic membrane 41 after which impression tray 42 carrying the impression 43 is placed on the plastic membrane 41. The impression tray 42 is permitted to settle into the quick set plaster 40 forming a stable support. The procedures are delayed sufficiently to permit the quick set plaster 40 to harden or arrive at a stable configuration.

OPERATION OF THE DEVICE

At this stage of the procedure the combination of this invention becomes particulrly self-evident to a dentist or skilled technician. In the following casting procedures, replicas of the individual teeth may be accurately produced. To accomplish this individual brass dowel pins 37 must be precisely positioned in the center of a tooth indentation 44 which is to be subjected to restoration procedures. Horizontal horseshoe magnet 33 is placed on first horizontal plate 19 with vertical horseshoe magnet 34 projecting over tooth indentation 44. Dowel support rod 36 carrying brass dowel pin 37 is placed in contact with vertical horseshoe magnet 34 and the magnets 33 and 34 shifted in position to the point wherein dowel support rod 36 is exactly in the center of tooth indentation 44. Dowel support rod 36 may be moved laterally, elevated or lowered to precisely place the brass dowel pin 37 in the center of the tooth indentation 44.

For an illustration of the flexibility afforded in positioning dowel pins utilizing the device, reference is particularly made to FIG. 1. In positioning the dowel support rod 36 carrying the brass dowel pin 37, it is rather self-evident that horizontal, horseshoe magnet 33 may be slid across and placed in any desired position on the face of the first horizontal plate 14. Dowel support rod 36 can be tilted at any desired angle from the vertical along the face of vertical, horseshoe magnet 34. The shifting of horizontal horseshoe magnet 33 on first horizontal plate 14 in combination with this shifting of dowel support rod 36 along the face of vertical horseshoe magnet 34 allows considerable latitude of positioning and angular adjustment. From the illustration of FIG. 1, it appears that it is quite possible to place dowel support rod 36 on the side of vertical, horseshoe magnet 34, thereby permitting a tilting of dowel support rod along the side of magnet 34. This selectively of positioning of dowel support rod 36 along the face or side of vertical horseshoe magnet 34 permits extensive latitude in laterally, vertically, and angularly positioning of the brass dowel pins 37 in the operation of the device of this invention. By the utilization of additional magnets and additional dowel support rods 36 other castings of individual teeth may be accomplished. With the dowel support rods 36 carrying the brass dowel pins 37 in the exact desired position the adjustable work table 19 is lowered to its bottom position and a first mix of stone 45 partially filling impression 43 is poured into position. Once this is accomplished the work table 19 is elevated to its exact former position by means of rotating the pinion knurled knobs 30 until reference pointer 16 contacts the upper surface of plastic top 20 which returns each component to the identical position the components were at the time the dowel support rods 36 and the brass dowel pins were adjusted into position. This first mix of stone 45 is permitted to set at which time it is coated with a releasing lubricant 46. At this point in the procedure the impression tray 42 carrying the impression 43 and the soldified first mix of stone 45 may be removed from the work table 19. The added second mix of stone 47 is placed on the impression 43 in the impression tray 42 forming the desired configuration for facility in handling and permitting to solidify. When the setting or curing process is completed the cast impression may be removed from the impression tray. The individual teeth which are to be the subject of restoration are separated from the remainder of the casting by saw cuts 48. With a saw cut 48 separating the individual tooth a tapping on the tip of dowel pin 37 will release the individual tooth from the casting. In pouring the second mix of stone 47 a slightly exposed tip 49 of the dowel pin 37 should remain visible. A tapping of this exposed tip 49 should release the individual tooth.

The procedures followed in the utilization of the device of this invention, although perhaps containing some degree of novelty when specifically applicable to the novel mechanical features of this invention, are not specifically claimed. The appended claims are mechanical in scope. What is desired to be claimed is all adaptations and modifications of the novel features of this invention not departing from the scope of equivalents of the invention as defined in the appended claims.

I claim:

1. A magnetic pin setter useful in dentistry being magnetically adjustable in three dimensions comprising:
   a. a metallic horizontal table supported above a base,
   b. an adjustable work table positioned below said horizontal table,
   c. a first magnet having its magnetically attaching surface magnetically slidably adjustable in a horizontal plane attached to said horizontal table,
   d. a second magnet spaced from said first magnet and having its magnetically attaching surface at right angles to the said magnetically attaching surface of said first magnet secured in a fixed, stable relationship by,
   e. a magnet connecting yoke retaining the said first magnet and said second magnet in predetermined spaced relationship,
   f. a dowel support rod magnetically attached to said second magnet, said dowel support rod being slidably adjustable vertically and tiltably adjustable at any desired angle in a plane along said magnetically attaching surface of said second magnet,
   g. a dowel pin frictionally attached to said dowel support rod,
   h. a substantially flat top attached to,
   i. a support stem,
   j. a ball and socket means swivelly retaining said support stem,
   k. an adjustable base secured to said ball and socket means for elevating and lowering said top further comprising:
      (1) an elevator base,
      (2) a ratchet shaft movably mounted in said elevator base, and
      (3) a rack and pinion drive means for elevating and lowering said ratchet shaft.

2. The invention of claim 1 wherein each of said magnets are horseshoe magnets.

3. The invention of claim 1 further comprising an impression tray supported in position on said adjustable work table.

4. The invention of claim 1 further comprising a second horizontal plate supported above said base.

5. The invention of claim 1 including a reference pointer restricting the elevation of said work table to assist in positioning said adjustable work table.

6. The invention of claim 1 further comprising:
   a. quick set plaster supported on the top of said work table, and
   b. an impression positioned in said impression tray supported by said plaster.

* * * * *